United States Patent [19]

Krueger

[11] Patent Number: 4,856,648

[45] Date of Patent: Aug. 15, 1989

[54] PACKAGING & INSTALLING IMPLANTS

[75] Inventor: Kenneth K. Krueger, Laguna Niguel, Calif.

[73] Assignee: Steri-Oss, Inc., Anaheim, Calif.

[21] Appl. No.: 140,255

[22] Filed: Dec. 31, 1987

[51] Int. Cl.⁴ .............................................. B65D 85/32
[52] U.S. Cl. ..................................... 206/63.5; 206/229
[58] Field of Search ............................... 206/63.5, 229

[56] References Cited

U.S. PATENT DOCUMENTS

| | | | |
|---|---|---|---|
| 3,378,925 | 4/1968 | Faller | 206/63.5 |
| 3,579,306 | 5/1971 | Crane | 206/229 |
| 3,703,977 | 11/1972 | Pisarek | 206/63.5 |
| 3,890,204 | 6/1975 | Avery | 206/229 |
| 4,364,473 | 12/1982 | Bogaert | 206/63.5 |

FOREIGN PATENT DOCUMENTS 427181 5/1911 France ................. 206/229

Primary Examiner—Joseph Man-Fu Moy
Attorney, Agent, or Firm—Grant L. Hubbard

[57] ABSTRACT

A dental implant can be packaged under sterile conditions so that it can be installed without being touched by using a two container type package. The primary container is sealed with a conventional cap so that its interior is sterile. It is used to hold a secondary container the interior of which is sterile and is sealed off using an easily removed closure. This closure is constructed so as to support the implant in such a manner that the closoure can be used as a holder in locating the implant in a desired location. The closure is constructed so that the implant can be easily removed from it when the implant has been so located.

10 Claims, 1 Drawing Sheet

PACKAGING & INSTALLING IMPLANTS

BACKGROUND OF THE INVENTION

The invention set forth in this specification pertains to both new and improved packages for implants which are intended to be used within a human body and to a new and improved process of installing such implants.

The term "implant" as used in this document is intended as a generic term designating any member or structure which is intended to be implanted or otherwise installed within the human body. Because of the intended utilization of any such implant it is extremely important that it be packaged under sterile conditions or sterilized immediately prior to use and that it be maintained sterile to a great an extent as is reasonably possible as it is located in desired location within a body. In order to minimize the possibility of an implant being contaminated it is considered that it is preferable to avoid physically handling an implant as much as is reasonably possible during the removal of the implant from sterile conditions such as are used in packaging it and during the installation of the implant.

These factors are easily illustrated by referring to the preferred utilization of the invention with dental implants. In the past such implants have been supplied to dental practitioners in packages the interiors of which have been sterilized and in non-sterile packages. In the latter case it is intended that the implant be sterilized prior to use. In both cases there is a possibility of the implant being contaminated as it is removed from sterile conditions and is located in an intended position in a mouth.

BRIEF SUMMARY OF THE INVENTION

It is believed that it will be apparent from the preceding discussion that there is a need for improvement in the manner in which implants are handled as they are removed from sterile conditions in a package and located in an intended location so as to minimize the chances of contamination as an implant is being so located. This invention is intended to provide a new and improved process for installing implants to remedy this need. It is intended to provide a process as indicated which may be easily and conveniently carried out with a minimum of difficulty.

The invention is also intended to provide new and improved packages for implants which are specifically adapted to be used in carrying out the process referred to in the preceding paragraph. More specifically it is intended to provide new and improved packages for implants which are relatively inexpensive, which can be easily opened so as to gain access to an implant and which are of such a character that a package as a "whole" and, in particular, part of the package can be used to avoid touching an implant or to minimize the amount an implant is touched as it is installed in a desired location.

Although the process of this invention and packages in accordance with this invention are at least in theory capable of being used in connection with a wide variety of different type of implants intended to be used in various locations in a body both this process and such packages in accordance with the invention are considered to be especially adapted to be used with dental implants. More specifically the invention is primarily intended to be used with dental implants of an elongated configuration having a shank or root-like portion which intended to be inserted into body tissue and a head which is adapted to be exposed in the mouth.

In accordance with this invention such a process is a process for maintaining sterile conditions during the installation of an implant in an intended location in the body of an intended user of the implant which comprises:

removing a secondary container from within the sterile interior of a primary sealed container, the secondary container having a sterile interior containing said implant which is closed off by a removable closure, said closure releasably supporting said implant within the interior of secondary container, removing said closure and said implant as a unit from said secondary container without said implant being touched, placing said implant in substantially a desired location in said body as said implant is supported by said closure so as to avoid touching said implant as it is placed within said location, and, manipulating said closure so as to release said implant from said closure after said implant is substantially in said location.

A package for use in carrying out a process as indicated in the preceding in accordance with this invention includes the combination of a container having an open end, an implant located within said container and a cap removably secured to said open end of said container, said cap closing off said open end of said container, the interior of said container being sterile, in which the improvement comprises:

a secondary container located within said first mentioned container, said secondary container having an open end and being capable of being removed from said first mentioned container through said open end of said first mentioned open container, a closure removably secured to said open end of said secondary container, said closure closing off said open end of said secondary container from the interior of said first mentioned container, an implant having a head which is adapted to be held as said implant is inserted in a desired location with a body located within said secondary container, said closure including holding means for temporarily holding said head when said closure is in place on said secondary closure and as said closure and said implant are removed from said secondary container as a unit and as said implant is located in substantially a desired position in a body.

BRIEF DESCRIPTION OF THE DRAWING

As a result of the character of the present invention it is considered that it is best more fully explained with reference to the accompanying drawing in which.

The accompanying drawing is intended to be used in explaining a presently preferred manner of practicing the process of this invention and a presently preferred package in accordance with this invention. Both this process and this package utilize operative concepts or principles as are set forth and defined in the appended claims forming a part of this specification. This skilled in the field of packaging and installing implants in a body will realize that the concepts or principles of this invention can be used in various manners than are precisely indicated in this specification through the use or exercise of routine skill in the noted field. For this reason the invention is to be considered as being limited solely by the appended claims.

DETAILED DESCRIPTION OF THE PREFERRED EMBODIMENT

Figure 1:
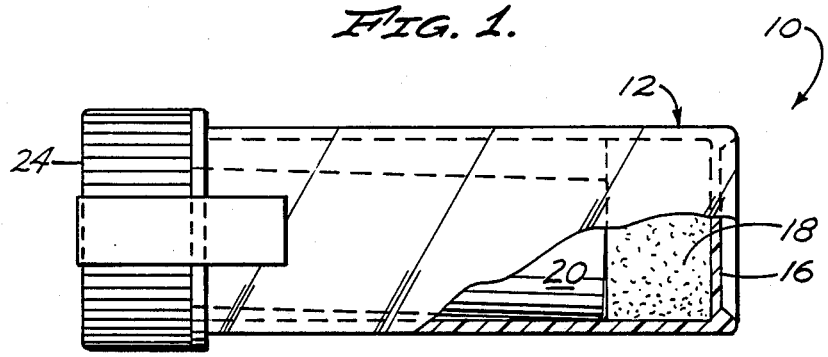
FIG. 1 is a side elevational view of a presently preferred embodiment in the form of a complete package in accordance with this invention, part of this view being broken away in order to expedite an understanding of a feature of this package.

In FIG. 1 of the drawing there is shown a complete package 10 in accordance with this invention. This package 10 includes a primary container 12 of a tubular cross-sectional configuration having an open top 14 and a bottom 16 located opposite the top 14. Preferably a small cylinder 18 of a resilient, elastomeric polymer foam is located within the container adjacent to the bottom 16. This cylinder 18 is used to resilient bias a secondary container 20 so that a closure 22 for it is biased against a conventional, easily removable cap 24 for the container 12.

Preferably this cap 24 is threaded on the container 12 as shown so that it cannot be inadvertently or easily removed from the container 12. This cap 24 is used to close off and seal the interior (not separately numbered) of the container 12 and, or course, the contents of this container 12 so as to continuously maintain sterile conditions within the container 12. Similarly the closure 22 is used to maintain sterile conditions within the secondary container 20. However, this closure 22 preferably differs from the cap 24 in several regards.

Figure 2:
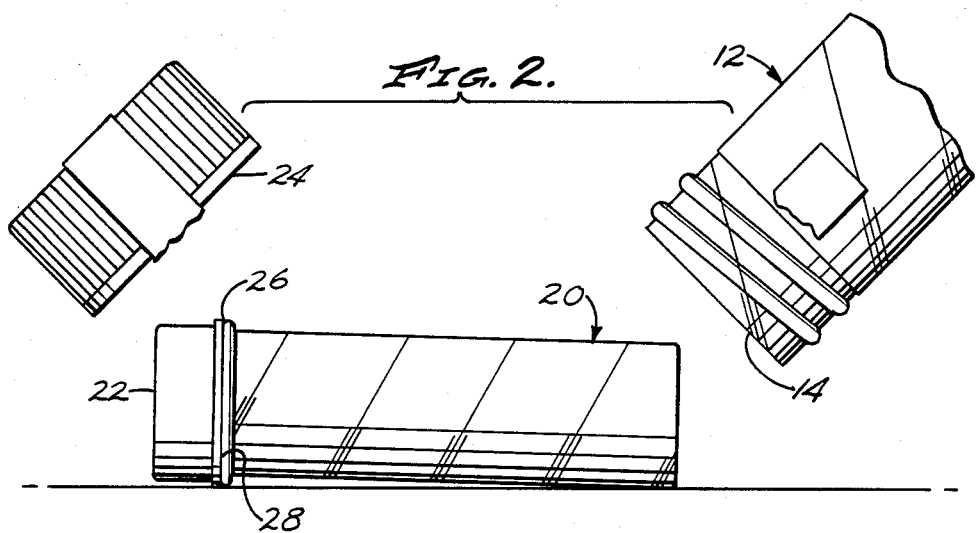
FIG. 2 is a side elevational view showing a step in gaining access to an implant packaged in package as shown in FIG. 1.
Figure 3:
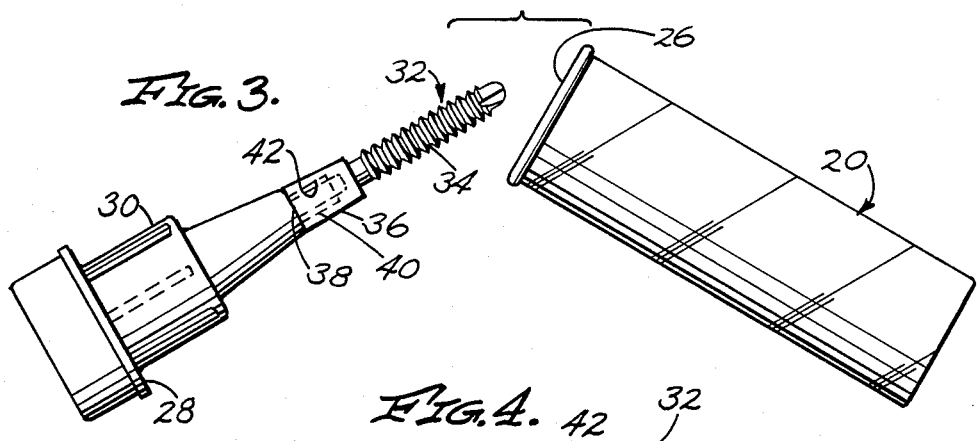
FIG. 3 is another side elevational view showing a further step of removing the implant from the package prior to the implant being located in substantially a desired location.
Figure 4:
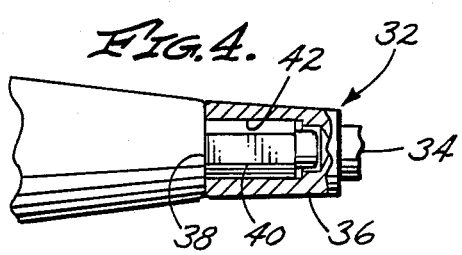
FIG. 4 is a partial side elevational view at an enlarged scale which is broken away so as to show how a holder or holding means on a closure is used to support a head on the implant.

It preferably is formed of an elastomeric material so that it can be pressed into a position as shown in FIG. 2 in order to seal off and maintain sterile conditions within the interior (not separately numbered) of the secondary container 20. If desired the press fit preferably used can be supplemented by the use of an easily frangible adhesive (not shown) generally between the top 26 of the container 20 and an undersurface or shoulder 28 of the closure 22 and a tapered, stopper-like stud or shank 30 of the closure 22. This press fit type of connection between the closure 22 and the secondary container 20 is considered preferable in as much it makes it possible to easily separate the closure 22 from the container 20 as an implant such as the implant 32 illustrated is being taken out of the package 10.

An implant such as the implant 32 packaged in the package 10 can, of course, be constructed in a number of different manners. Normally such an implant will be formed so as to include an elongated shank 34 and a head 36. When the implant 32 is in a preferred manner this shank 34 will be shaped so as to be especially adapted to be implanted in the oral cavity of a human body in such a manner that only the top 38 of the head 36 is exposed.

In order to minimize the chances of th implant 32 being contaminated during its installation, the closure 22 is constructed so as to include a non-round projection 40 which is dimensioned to frictionally fit with a correspondingly shaped non-round socket 42 within the top 38 of the head 36 of the implant in such a manner that the entire implant 32 is normally supported so that it and the closure 22 can be withdrawn from the secondary container 22 and moved together as a unit. When the implant 32 is supported in this manner the closure 22 can normally be manipulated so as to easily release the implant 32 after it ahs been installed in substantially a desired location. Preferably the amount of friction holding the implant 32 in place on the closure 22 is quite limited so that the implant 32 will nearly fall off of the projection 40 as the implant 32 is being installed in an intended location.

As will be obvious prior to its use the entire package 10 will be assembled with the implant 32 in the secondary container 20 and with the latter in place within the primary container 12 as shown in FIG. 1, everything within or exposed to the interior (not separately numbered) of the container 12 will normally be sterilized in a conventional manner. When the package 10 is assembled in this manner the secondary container 20 will be more or less cushioned by the cylinder 18 against inadvertent movement. The package 10 when assembled noted in this discussion will appear as indicated in FIG. 1 and can be shipped prior to the implant 32 being used.

When the implant 32 is to be used normally the person using it will remove the cap 24 from the container 12. Next the container 12 will normally be manipulated so that the secondary container 20 falls on a sterile surface or so that the closure 22 can be digitally engaged and removed from the container 12. In either event the closure 22 will normally be next held by the hand of the user to be used in locating the implant 32 in a desired location and the container 20 will be separated from the closure 22 through the use of the other hand of the user. As this is done normally is will be preferable to hold the closure 22 so that the implant 32 is pointed more or less upwardly as much as possible to avoid any possibility of the implant falling off of the projection 40.

When the implant 32 is free of the container 20 it may be located in a desired position or substantially in a desired position within an oral cavity without being touched by manipulating the closure 22 so that the latter is used as a temporary holder. At the time the implant 32 is in such a desired position normally the closure 22 can usually be removed from it without the implant 32 being touched by a simple manipulative action since there will usually be a minor amount of engagement between the shank 34 and the body sufficient to overcome the force holding the implant 32 on the projection 40. During such manipulation no contamination will result from the closure 22 contacting any area or object as a result of the fact that it is sterile.

I claim:

1. A process for maintaining sterile conditions during the installation of an implant in an intended location in the body of an intended user of the implant comprising the steps of:

removing a secondary container from within the sterile interior of a primary sealed container, the secondary container having a sterile interior containing said implant closed off by a removable closure, said closure releasably supporting said implant within the interior of said secondary container, removing said closure and said implant as a unit from said secondary container without said implant being touched, placing said implant in substantially a desired location in said body as said implant is supported by said closure so as to avoid handling said implant as it is placed within said location, and manipulating said closure so as to release said implant from said closure after said implant is substantially in said location.

2. A process as claimed in claim 1 wherein:

said implant is a dental implant having a head and a shank, and said head of said implant is supported by said closure.

3. A process as claimed in claim 2 wherein;

said head has a top which is adapted to be exposed in the oral cavity of said body, said top of said head including means engaged by said closure so as to support said implant.

4. A process as claimed in claim 3 wherein:

said means is a socket, and said closure includes a projection frictionally fitting within said socket.

5. In the combination of a container having an open end, an implant located within said container and a cap removably secured to said open end of said container, said cap closing off said open end of said container, the interior of said container being sterile, the improvement comprising:

a secondary container located within said first mentioned container, said secondary container having an open end and being capable of being removed from said first mentioned container through said open end of said first mentioned open container, a closure removably secured to said open end of said secondary container, said closure closing off said open end of said secondary container from the interior of said first mentioned container, an implant having a head which is adapted to be held as said implant is inserted in a desired location within a body, said implant being located within said secondary container, and said closure including holding means for temporarily holding said head when said closure is in place on said secondary closure and as said closure and said implant are removed from said secondary container as a unit and as said implant is located in substantially a desired position in a body.

6. An apparatus as claimed in claim 5 wherein:

said closure is removably secured to said secondary container by being frictionally attached to said container.

7. An apparatus as claimed in claim 6 wherein:

said head includes a top which is expected to be exposed, and said closure engages said top.

8. An apparatus as claimed in claim 7 wherein:

said head includes an internal socket means in said top, and said closure includes a projection frictionally fitting within said socket.

9. An apparatus as claimed in claim 8 wherein:

said socket is of a non-round cross-sectional configuration, and said projection is of a complementary non-round cross-sectional configuration.

10. An apparatus as claimed in claim 5 wherein:

said closure is removably secured to said secondary container by being frictionally attached to said container, said head includes a top which is expected to be exposed, said closure engages said top, said head includes an internal means in said top, said closure includes a projection frictionally fitting within said socket, said socket is of a non-round cross-sectional configuration, and said projection is of a complementary non-round cross-sectional configuration.

* * * * *